(12) United States Patent
Yoshida et al.

(10) Patent No.: US 7,988,358 B2
(45) Date of Patent: Aug. 2, 2011

(54) X-RAY FLUOROSCOPIC APPARATUS

(75) Inventors: Koji Yoshida, Kyoto (JP); Takuji Shishikura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 12/516,189

(22) PCT Filed: Nov. 24, 2006

(86) PCT No.: PCT/JP2006/323429
§ 371 (c)(1),
(2), (4) Date: May 22, 2009

(87) PCT Pub. No.: WO2008/062531
PCT Pub. Date: May 29, 2008

(65) Prior Publication Data
US 2010/0020939 A1    Jan. 28, 2010

(51) Int. Cl.
*H05G 1/02*    (2006.01)
(52) U.S. Cl. ....................................................... 378/197
(58) Field of Classification Search .................. 378/196, 378/197, 198
See application file for complete search history.

(56) References Cited

U.S. PATENT DOCUMENTS
2002/0051517 A1 *  5/2002  Schwieker .................... 378/196

FOREIGN PATENT DOCUMENTS
| JP | 4-164437 A | 6/1992 |
| JP | 2001-333892 A | 12/2001 |
| JP | 2005-287668 A | 10/2005 |

OTHER PUBLICATIONS
International Search Report for the Application No. PCT/JP2006/323429 mailed Feb. 20, 2007.

* cited by examiner

*Primary Examiner* — Chih-Cheng G Kao
(74) *Attorney, Agent, or Firm* — Cheng Law Group, PLLC

(57) ABSTRACT

The X-ray fluoroscopic apparatus of this invention includes a slide arm for supporting an X-ray tube, a middle slider for holding the support arm to be movable in directions along an irradiation axis of the X-ray source, and a strut for holding the middle slider to be movable the directions along the irradiation axis. Thus, compared with an amount of stroke of the X-ray tube, an amount of movement of each of the middle slider and the support arm can be small, and each of the strut, middle slider and support arm can be shortened to reduce apparatus height. Therefore, the amount of stroke of the X-ray source can be secured appropriately, while inhibiting an increase in installation space.

7 Claims, 11 Drawing Sheets

X-RAY FLUOROSCOPIC APPARATUS

TECHNICAL FIELD

This invention relates to an X-ray fluoroscopic apparatus for fluoroscoping a patient, and more particularly to a technique for moving an X-ray source toward and away from an imaging device.

BACKGROUND ART

There are X-ray fluoroscopic apparatus for enabling, in addition to diagnosis of the alimentary canal including the stomach, also X-ray radiography of the chest. However, it is necessary to secure a longer distance from an X-ray source to an imaging device (hereinafter called FFD: Focus Film Distance as appropriate) at a time of chest radiography than at a time of alimentary canal diagnosis. For example, it is about 1.8 to 2.0 m in the case of chest radiography, as opposed to 1.1 m in the case of alimentary canal diagnosis. FIG. 10 shows a conventional X-ray fluoroscopic apparatus constructed to be capable of such multipurpose fluoroscopy. FIG. 10 shows front views of the conventional X-ray fluoroscopic apparatus, in which (a) shows a state of a top board being horizontal, (b) shows a state of the top board being inclined, and (c) shows a state of the top board being vertical. As shown, the conventional apparatus includes a tiltable top board 61 for supporting a patient M, an X-ray tube 63 disposed above the top board 61, a cassette 65 disposed below the top board 61 to be opposed to the X-ray tube 63 and loaded with a film, a strut 67 for supporting the cassette 65, and a support arm 69 extendible and retractable relative to the strut 67 for holding the X-ray tube 63. The top board 61 is held by a top board support (main frame) 71, and the main frame 71 is supported by a pedestal 77 to be rockable through a pinion 73 and sector rack 75. The top board 61 tilts up and down by rotating with the main frame 71. The strut 67 is supported through a drive mechanism, not shown, mounted in the main frame 71, to be movable longitudinally of the top board 61 by the drive mechanism and rotatable with the main frame 71. The X-ray tube 63 has a collimator 81 attached thereto. In an alimentary canal diagnosis using the conventional X-ray fluoroscopic apparatus constructed in this way, fluoroscopy is carried out with the support arm 69 retracted to shorten the focus film distance. At this time, as shown in FIGS. 10 (a) and (b), the top board 61 is usually tilted with a patient M placed thereon. In a chest radiography, radiograms are taken with the support arm 69 extended to lengthen the focus film distance. At this time, as shown in FIG. 10 (c), the patient M usually takes a standing position (see Patent Document 1, for example).

[Patent Document 1]
Unexamined Patent Publication No. 2005-287668

DISCLOSURE OF THE INVENTION

Problem to be Solved by the Invention

However, when an amount of sliding of the support arm 69 is increased in order to secure a sufficient amount of stroke of the X-ray tube 63, there occurs an inconvenience of enlarging installation space. Conversely, when installation space is reduced, the amount of sliding of the support arm 69 will become small, which brings about an inconvenience that multipurpose fluoroscopy cannot be carried out appropriately.

This will be described specifically with reference to FIG. 11. FIG. 11 shows side views of the strut and support arm according to the prior art, in which (a) shows a state of the support arm being retracted, and (b) a state of the support arm being extended. As shown in FIGS. 11 (a) and (b), between the strut 67 and support arm 69, a guide mechanism is provided which includes a guide rail 91 and a plurality of slide blocks 93. Here, in order to fully secure an amount of stroke of the X-ray tube 63, the top of the support arm 69 is made higher than the X-ray tube 63 to increase the amount of sliding of the support arm 69 relative to the strut 67. In this case, the height of the apparatus is increased by an amount corresponding to the amount (i.e. the distance affixed with sign "L" in the drawings) by which the support arm 69 is made higher than the X-ray tube 63, thereby enlarging installation space for permitting tilting of the top board 61.

A restraint on apparatus height will entail a reduction in the amount of sliding of the support arm 69 relative to the strut 67, thereby failing to secure a sufficient amount of stroke of the X-ray tube 63. As a result, for example, when the focus film distance cannot be lengthened, a blur will occur with images obtained, which will make proper chest radiography impossible. When the focus film distance cannot be shortened, alimentary canal diagnosis cannot be carried out appropriately.

This invention has been made having regard to the state of the art noted above, and its object is to provide an X-ray fluoroscopic apparatus capable of appropriately securing an amount of stroke of an X-ray source while inhibiting an increase in installation space.

Means for Solving the Problem

To fulfill the above object, this invention provides the following construction.

An X-ray fluoroscopic apparatus of this invention is an X-ray fluoroscopic apparatus for fluoroscoping a patient, comprising an X-ray source for emitting X rays to the patient; a support arm for supporting the X-ray source; a middle slider for holding the support arm to be movable along an irradiation axis of the X-ray source; and a strut for holding the middle slider to be movable along the irradiation axis.

According to the X-ray fluoroscopic apparatus of this invention, each of the middle slider and the support arm is movable along the irradiation axis. Thus, the amount of movement (hereinafter called the amount of stroke as appropriate) along the irradiation axis of the X-ray source corresponds to a sum total of amounts of movement of the middle slider and the support arm. That is, compared with the amount of stroke of the X-ray source, an amount of movement of each of the middle slider and the support arm can be small, and each of the strut, middle slider and support arm can be shortened to reduce apparatus height. Therefore, the amount of stroke of the X-ray source can be secured appropriately, while inhibiting an increase in installation space.

In the X-ray fluoroscopic apparatus of this invention, it is preferred that the strut has two legs formed like ridges thereon to extend along the irradiation axis for holding the middle slider with the legs, the support arm being insertable into a groove formed between the legs. Without reducing rigidity, the support arm can be retracted compactly.

In the X-ray fluoroscopic apparatus of this invention, it is preferred that the support arm has a top portion lower than a height of the X-ray source supported by the support arm. This can curb installation space.

Preferably, the X-ray fluoroscopic apparatus of this invention further comprises a first guide mechanism provided between the strut and the middle slider for guiding the middle slider along the irradiation axis relative to the strut, and a second guide mechanism provided between the middle slider and the support arm for guiding the support arm along the irradiation axis relative to the middle slider. The middle slider and support arm can be slid conveniently through the first and second guide mechanisms.

Preferably, the X-ray fluoroscopic apparatus of this invention further comprises a first drive device for moving the middle slider along the irradiation axis relative to the strut, and a second drive device for moving the support arm along the irradiation axis relative to the middle slider. With the first and second drive devices, the middle slider and support arm can be moved easily.

In the X-ray fluoroscopic apparatus of this invention, it is preferred that the middle slider has a plurality of split slide members, the split slide members being connected to each other to be movable along the irradiation axis, such that a space between a position where the strut holds the middle slider and a position where the middle slider holds the support arm is extendible and contractible. With the middle slider itself constructed telescopic, the amount of stroke of the X-ray source is a sum total of the amount of movement of the support arm, the amount of movement of the middle slider relative to the strut, and the amount of expansion and contraction of the middle slider itself. As a result, the amount of stroke of the X-ray source can be further increased, while curbing installation space.

In the X-ray fluoroscopic apparatus of this invention, it is preferred that the strut is rotatable about a horizontal axis. Then, an alimentary canal diagnosis, chest radiography and the like can each be carried out conveniently.

This specification discloses also the invention relating to the following X-ray fluoroscopic apparatus:

(1) In the X-ray fluoroscopic apparatus according to this invention, the first guide mechanism preferably includes first guide rails provided on one of the strut and the middle slider, and first slide blocks provided on the other of the strut and the middle slider to be slidable along the first guide rails, and the second guide mechanism includes second guide rails provided on one of the middle slider and the support arm, and second slide blocks provided on the other of the middle slider and the support arm to be slidable along the second guide rails.

According to the invention set out in (1) above, the first and the second guide mechanisms are realized conveniently.

(2) In the X-ray fluoroscopic apparatus according to this invention, the strut preferably further supports an imaging device in a position opposed to the X-ray source for detecting and imaging X rays transmitted through the patient.

According to the invention set out in (2) above, the X-ray source and imaging device can be moved together as opposed to each other.

(3) The X-ray fluoroscopic apparatus according to this invention preferably further comprises an imaging support device for movably supporting the imaging device, the imaging device being movable independently of the X-ray source.

According to the invention set out in (3) above, the position relative to the imaging device of the irradiation axis of the X-ray source can be moved. This allows chest radiography to be carried out conveniently.

(4) The X-ray fluoroscopic apparatus according to this invention preferably further comprises a first projection provided on one of the strut and the middle slider, and first restrictors provided on the other of the strut and the middle slider to be capable of contacting the first projection, for limiting a moving range of the middle slider relative to the strut, and a second projection provided on one of the middle slider and the support arm, and second restrictors provided on the other of the middle slider and the support arm to be capable of contacting the second projection, for limiting a moving range of the support arm relative to the middle slider.

According to the invention set out in (4) above, it is possible to prevent effectively the middle slider from falling off the strut, and the support arm from falling off the middle slider.

Effects of the Invention

According to the X-ray fluoroscopic apparatus of this invention, each of the middle slider and the support arm is movable along the irradiation axis. Thus, the amount of stroke of the X-ray source corresponds to a sum total of amounts of movement of the middle slider and the support arm. That is, compared with the amount of stroke of the X-ray source, an amount of movement of each of the middle slider and the support arm can be small, and each of the strut, middle slider and support arm can be shortened to reduce apparatus height. Therefore, the amount of stroke of the X-ray source can be secured appropriately, while inhibiting an increase in installation space.

DESCRIPTION OF REFERENCES

Figure 1:
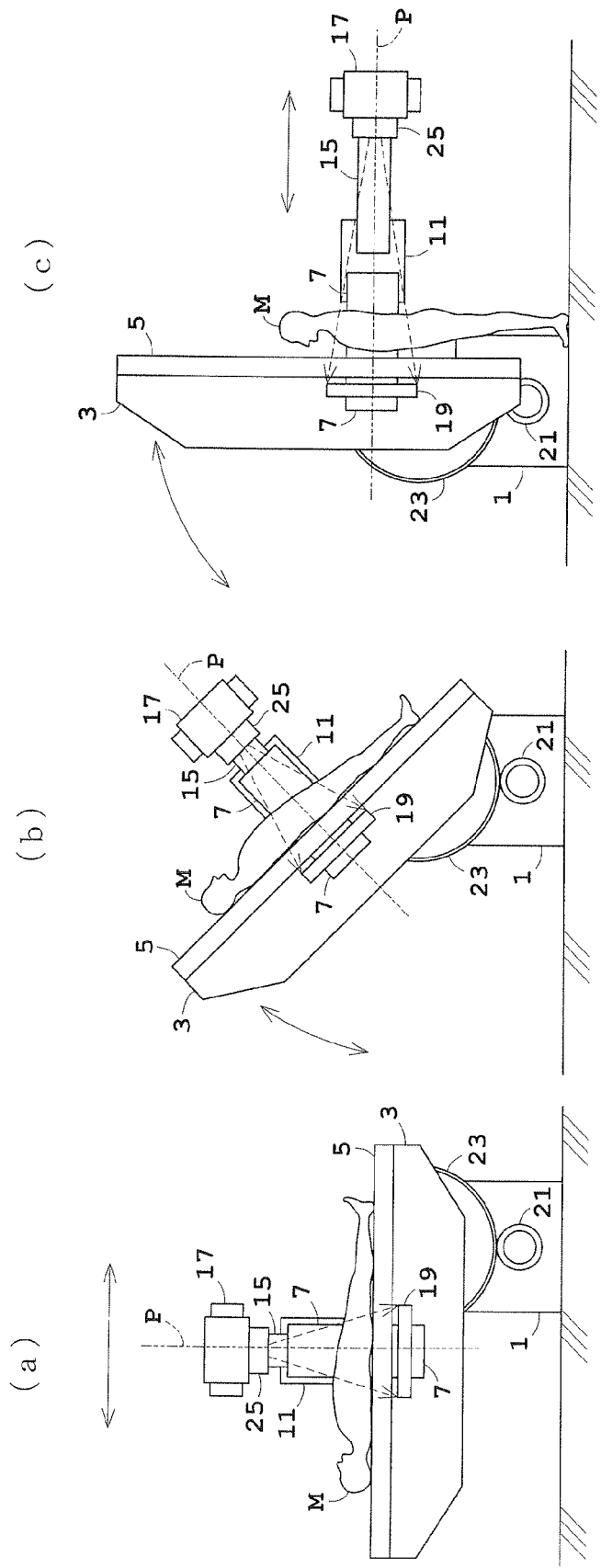
FIG. 1 shows front views of an X-ray fluoroscopic apparatus according to an embodiment, in which (a), (b) and (c) show horizontal, inclined and vertical states of a top board, respectively.

5 . . . top board
7 . . . strut
11, 12, 13, 14 . . . middle sliders
14a, 14b . . . split slide members
15 . . . support arm
17 . . . X-ray tube
19 . . . cassette
31 . . . legs
33 . . . first guide rails
35 . . . first slide blocks
37 . . . second guide rails
39 . . . second slide blocks
41 . . . first projection
43 . . . first restrictors
45 . . . second projection
47 . . . second restrictors
51 . . . first gear
52 . . . first motor
53 . . . first rack
55 . . . second gear
56 . . . second motor
57 . . . second rack
M . . . patient
P . . . irradiation axis
A . . . groove

BEST MODE FOR CARRYING OUT THE INVENTION

In an X-ray fluoroscopic apparatus for fluoroscoping a patient, which includes an X-ray source for emitting X rays to the patient, a support arm for supporting the X-ray source, a middle slider for holding the support arm to be movable in directions along an irradiation axis of the X-ray source, and a strut for holding the middle slider to be movable in the directions along the irradiation axis. This construction has fulfilled the object of appropriately securing an amount of stroke of the X-ray source while inhibiting an increase in installation space.

Embodiment 1

Embodiment 1 of this invention will be described hereinafter with reference to the drawings. FIG. 1 shows front views of an X-ray fluoroscopic apparatus according to the embodiment. In FIG. 1, (a), (b) and (c) show horizontal, inclined and vertical states of a top board, respectively.

The X-ray fluoroscopic apparatus according to this embodiment includes a pedestal 1, a top board support (hereinafter referred to simply as the main frame) 3, a top board 5, a strut 7, a middle slider 11, a support arm 15, an X-ray tube 17 and a cassette 19. The pedestal 1 is installed on a floor, and has a pinion 21 rotatable about a horizontal axis by a drive mechanism not shown. The main frame 3 has a sector rack (gear) 23 meshed with the pinion 21, is supported by the pedestal 1, and is rotatable about a horizontal axis by rotation of the pinion 21. The top board 5 is held by the main frame 3 to be tiltable with rotation of the main frame 3. The strut 7 is supported by the main frame 3 through a drive mechanism not shown, to be movable forward and backward longitudinally of the top board 5 by this drive mechanism, and rotatable about the horizontal axis with rotation of the main frame 3. The support arm 15 is L-shaped. The support arm 15 is supported at a proximal end thereof by the middle slider 11 to be movable in directions perpendicular to the top board 5. The X-ray tube 17 is attached to the distal end of the support arm 15 so that the irradiation axis P which is the central axis of an X-ray beam emitted may extend perpendicular to the top board 5. This X-ray tube 17 has a collimator 25 attached thereto. The cassette 19 is held by the strut 7 in a position below the top board 5 and opposed to the X-ray tube 17. The cassette 19 is loaded with a film (not shown). The X-ray tube 17 and cassette 19 correspond to the X-ray source and imaging device in this invention, respectively.

Figure 2:
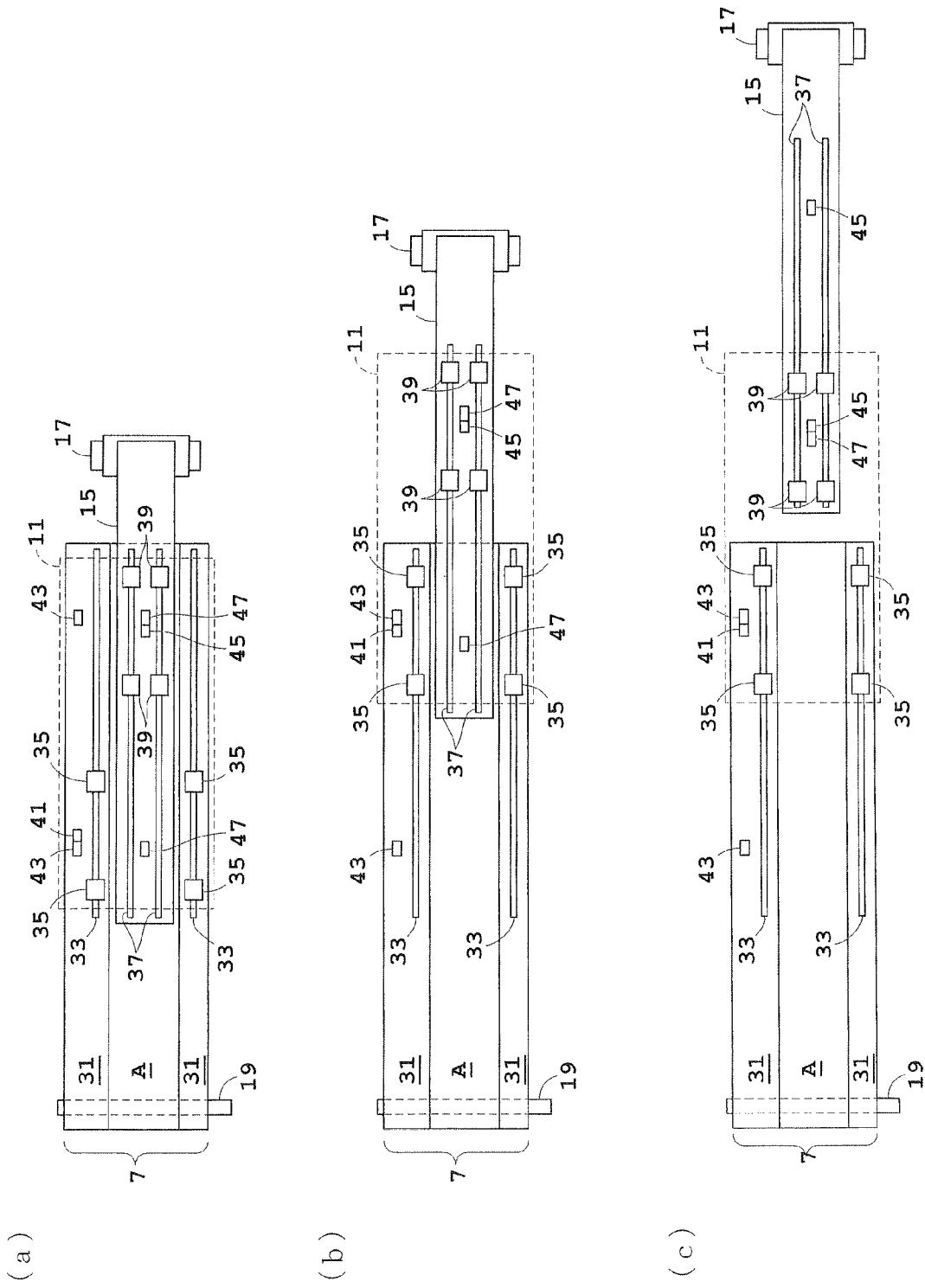
FIG. 2 shows front views of a strut, a middle slider and a support arm, in which (a) shows a state of the middle slider and support arm being retracted, (b) shows a state of the middle slider being extended and the support arm being retracted, and (c) shows a state of the middle slider and support arm being extended.
Figure 3:
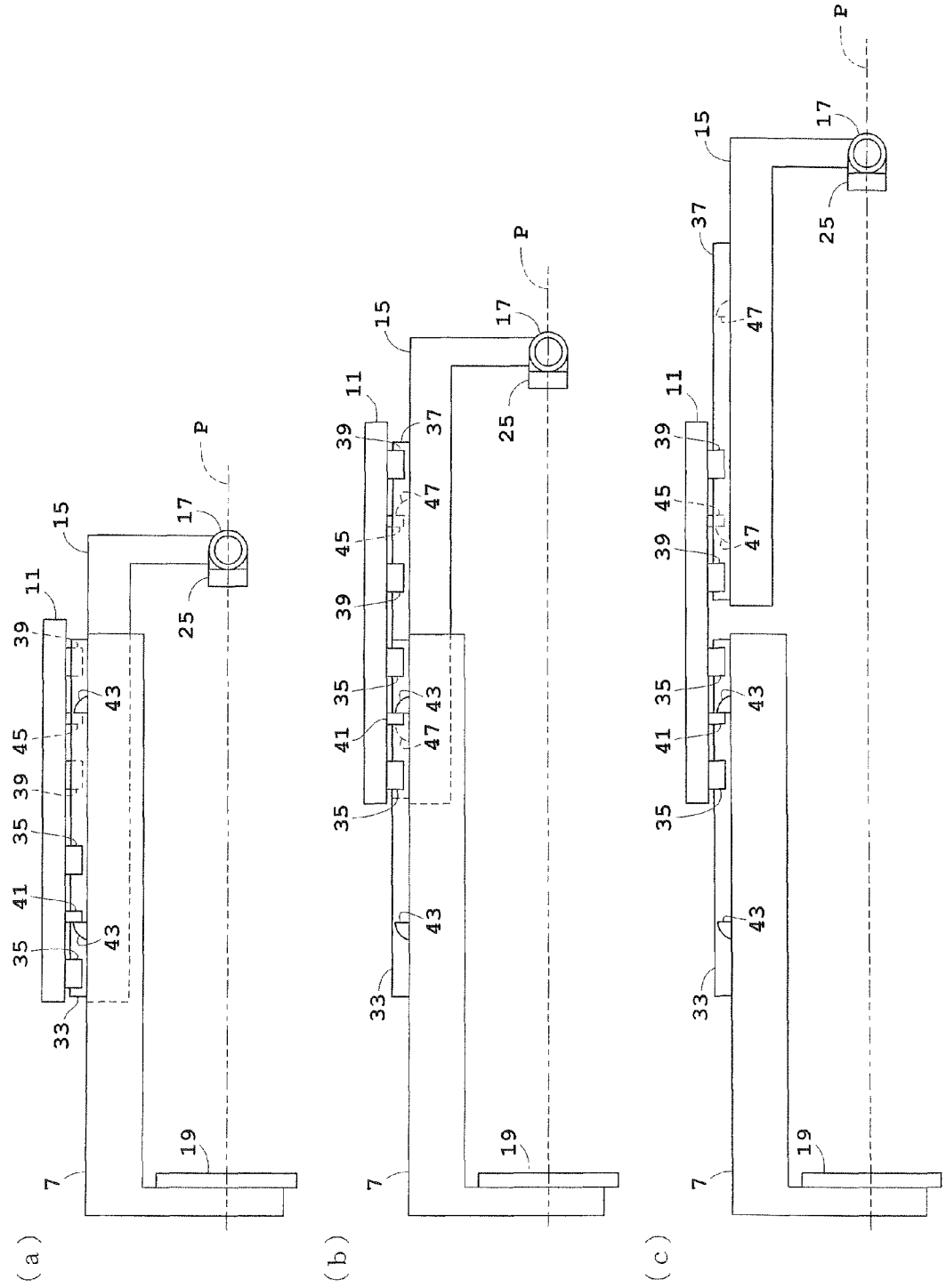
FIG. 3 shows side views of the strut, middle slider and support arm, in which (a) shows the state of the middle slider and support arm being retracted, (b) shows the state of the middle slider being extended and the support arm being retracted, and (c) shows the state of the middle slider and support arm being extended.
Figure 4:
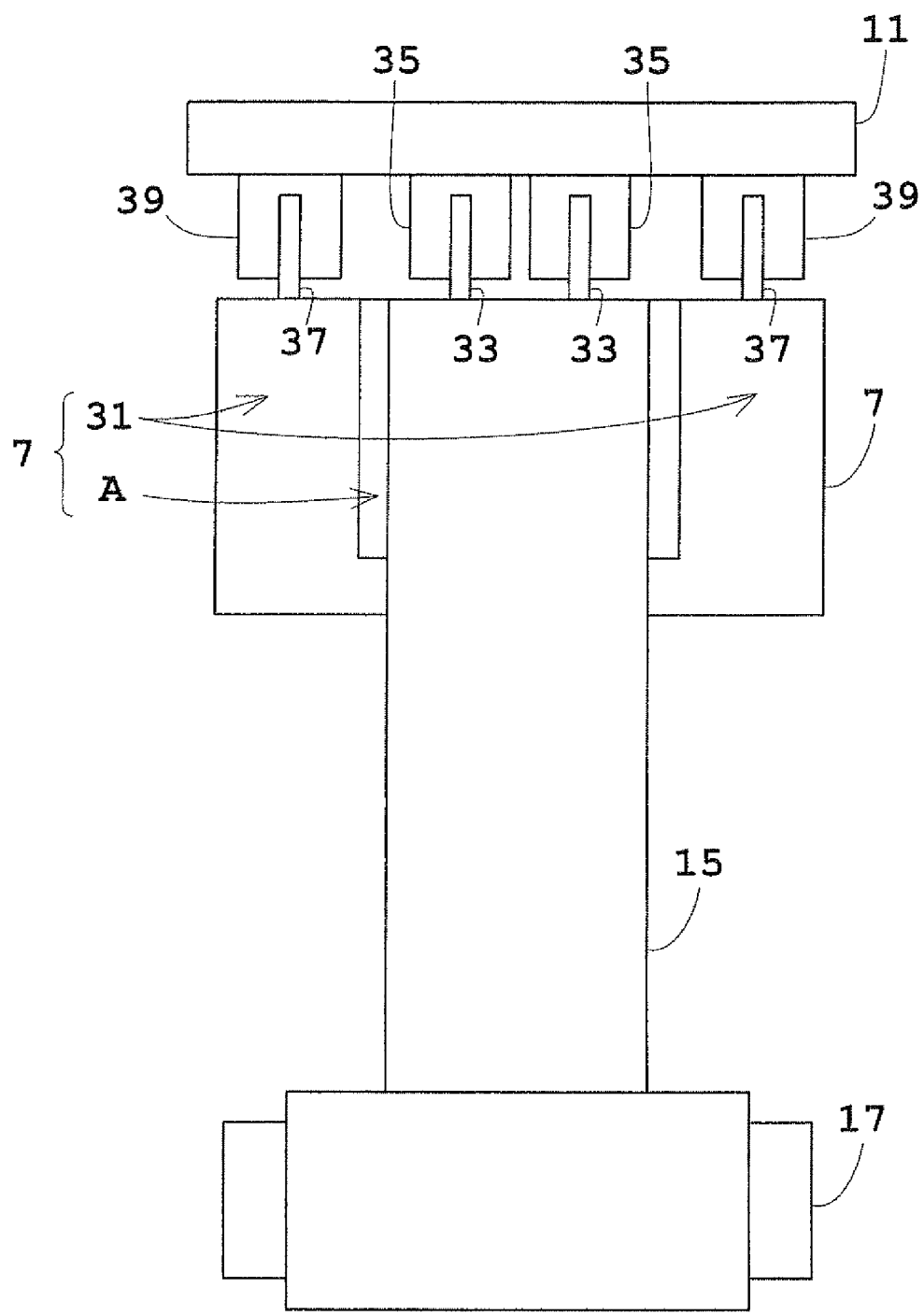
FIG. 4 is a sectional view of the strut, middle slider and support arm.
Figure 5:
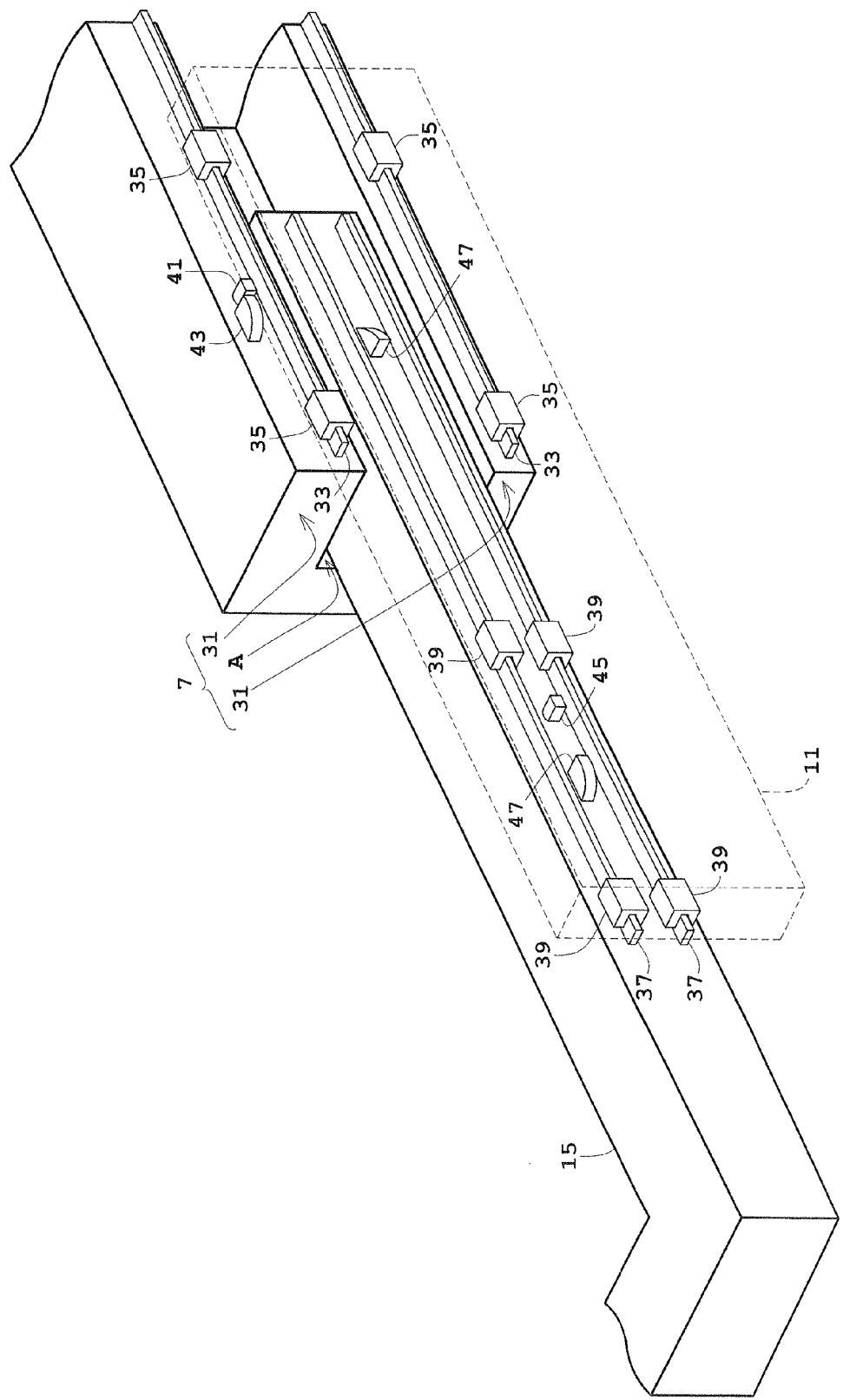
FIG. 5 is a perspective view of the strut, middle slider and support arm.

Next, the strut 7, middle slider 11 and support arm 15 will be described in detail. FIGS. 2, 3, 4 and 5 show front views, side views, a sectional view and a perspective view of the strut, middle slider and support arm, respectively. In FIGS. 2 and 3, (a) shows a state of the middle slider and support arm being retracted, (b) shows a state of the middle slider being extended and the support arm being retracted, and (c) shows a state of the middle slider and support arm being extended. In FIGS. 2, 3 and 5, the middle slider is shown in dotted lines.

As shown, the strut 7 has a groove A formed in one side thereof to extend along the irradiation axis P of X rays, and two legs 31 formed at opposite sides of this groove A to extend in the form of ridges. The strut 7 in this embodiment has a sectional shape resembling letter "U". The legs 31 have first guide rails 33 opposed to each other and extending parallel to the irradiation axis P. Each of these first guide rails 33 has first slide blocks 35 slidably attached thereto. In this embodiment, each first guide rail 33 has two first slide blocks 35. All the first slide blocks 35 are fixed to the middle slider 11, whereby the middle slider 11 is slidable relative to the strut 7. The first guide rails 33 and first slide blocks 35 will hereinafter be called the first guide mechanism as appropriate.

The support arm 15 has a proximal region thereof with a sectional shape slightly smaller than the sectional shape of the groove A to be accommodatable in the groove A. The support arm 15 has two second guide rails 37 attached to one side of the proximal region thereof, to be opposed to each other and extend parallel to the first guide rails 33. Each of the second guide rails 37 also has two second slide blocks 39 attached thereto. The second slide blocks 39 also are fixed to the middle slider 11, whereby the support arm 15 is slidable relative to the middle slider 11. The second guide rails 37 and second slide blocks 39 will hereinafter be called the second guide mechanism as appropriate.

Further, the middle slider 11 has a first projection 41 formed in a position opposed to the leg 31. In a corresponding relation thereto, the leg 31 has first restrictors 43 for contacting the first projection 41 in positions where the middle slider 11 is retracted and extended relative to the strut 7, respectively, to limit a moving range of the middle slider 11. Similarly, the middle slider 11 has a second projection 45 formed in a position opposed to the support arm 15. The support arm 15 has second restrictors 47 formed in the proximal region thereof for contacting the second projection 45 in positions where the support arm 15 is retracted and extended relative to the middle slider 11, respectively, to limit a moving range of the support arm 15. These first and second projections 41 and 45 and first and second restrictors 43 and 47 are appropriately arranged to obtain desired focus film distances.

Next, operation of the X-ray fluoroscopic apparatus according to Embodiment 1 will be described. When fluoroscopy is carried out with a shortened focus film distance as in alimentary canal diagnosis, the operator moves the middle slider 11 and support arm 15 toward the strut 7 (in the direction to approach the top board 5). The middle slider 11 and support arm 15 slide as guided by the first and second guide rails 33 and 37, respectively. When the first projection 41 contacts the first restrictor 43, the middle slider 11 will stop, and no further movement in this direction will be restricted. Similarly, when the second projection 45 contacts the second restrictor 47, the support arm 15 will stop, and no further movement in this direction will be restricted. In this way, the middle slider 11 moves to a position retracted relative to the strut 7, and moves the support arm 15 to a position retracted relative to the middle slider 11. At this time, the proximal region of the support arm 15 is inserted in the groove A formed between the two legs 31. The X-ray tube 17 and cassette 19 are in a positional relationship to realize a desired focus film distance (see (a) and (b) of FIGS. 2 and 3).

In this state, the pedestal 1 rotates the main frame 3, whereby the top board 5 with the patient M placed thereon and the strut 7 rock with the main frame 3 about the horizontal axis. As a result, the position of the patient M rotates about the horizontal axis. Based on instructions of the operator, the strut 7 moves longitudinally of the top board 5 as appropriate, to move the irradiation field of the X-ray tube 17 to a site of interest of the patient M. Then, the X-ray tube 17 emits X rays on instructions of the operator. The film in the cassette 19 detects X rays transmitted through the patient M. Such fluoroscopy is carried out for the site of interest of the patient M, while changing the position of the patient M as appropriate.

When fluoroscopy is carried out with a lengthened focus film distance as in chest radiography, the middle slider 11 and support arm 15 are moved away from the top board 5. The middle slider 11 slides along the first guide rails 33 relative to the strut 7, and stops in a position where the first projection 41 contacts the first restrictor 43. The support arm 15 slides along the second guide rails 37 relative to the middle slider 11, and stops in a position where the second projection 45 contacts the second restrictor 47. In this way, the middle slider 11 moves to a position extended relative to the strut 7, and moves the support arm 15 to a position extended relative to the middle slider 11. At this time, the X-ray tube 17 and cassette 19 are in a positional relationship to realize a desired focus film distance (see (c) of FIGS. 2 and 3).

Then, the strut 7 is moved longitudinally of the top board 5 as appropriate to carry out fluoroscopy. As shown in FIG. 1 (c), in chest radiography, the top board 5 usually is erected to be vertical, and X rays are emitted horizontally to the patient M in a standing position.

Thus, according to the X-ray fluoroscopic apparatus in this embodiment, since the middle slider 11 and support arm 15 move along the irradiation axis P, respectively, the X-ray tube 17 moves toward and away from the cassette 19 by a distance corresponding to the sum of their amounts of movement. Therefore, compared with the amount of stroke of the X-ray tube 17 (moving distance the X-ray tube 17 moves forward and backward along the irradiation axis), the amount of movement of each of the middle slider 11 and support arm 15 is small. Consequently, each of the strut 7, middle slider 11 and support arm 15 can be reduced in length. Since the top of the support arm 15 can be made lower than the height of the X-ray tube 17, it is not necessary to have a member higher than the height of the X-ray tube 17, like the support arm included in the X-ray fluoroscopic apparatus according to the prior art. Therefore, the amount of stroke of the X-ray tube 17 can be secured appropriately, while curbing apparatus height and inhibiting an increase in installation space.

The strut 7 holds the middle slider 11 with the two legs 31 formed along the irradiation axis P, and the support arm 15 is constructed insertable in the groove A formed between the two legs 31. Thus, without reducing the rigidity of the strut 7, the support arm 15 can be accommodated compactly in the groove A when the support arm 15 is retracted.

The first guide mechanism is provided between the strut 7 and middle slider 11, and the second guide mechanism between the middle slider 11 and support arm 15. This allows the middle slider 11 and support arm 15 to be slidable appropriately. With the first and second guide mechanisms having the first and second guide rails 33 and 37 and first and second slide blocks 35 and 39, the operator can easily slide the middle slider 11 and support arm 15.

Since the strut 7 is constructed rotatable about the horizontal axis, the patient M can be fluoroscoped from any angles.

Since the strut 7 holds the X-ray tube 17 and cassette 19 as opposed to each other, the opposed relationship of the X-ray tube 17 and cassette 19 is invariable even when the strut 7 moves longitudinally of the top board 5 or rotates about the horizontal axis. Thus, fluoroscopy can be carried out conveniently.

The first and second projections 41 and 45 and the first and second restrictors 43 and 47 provided can prevent the middle slider 11 from falling off the strut 7, and the support arm 15 from falling off the middle slider 11.

Figure 6:
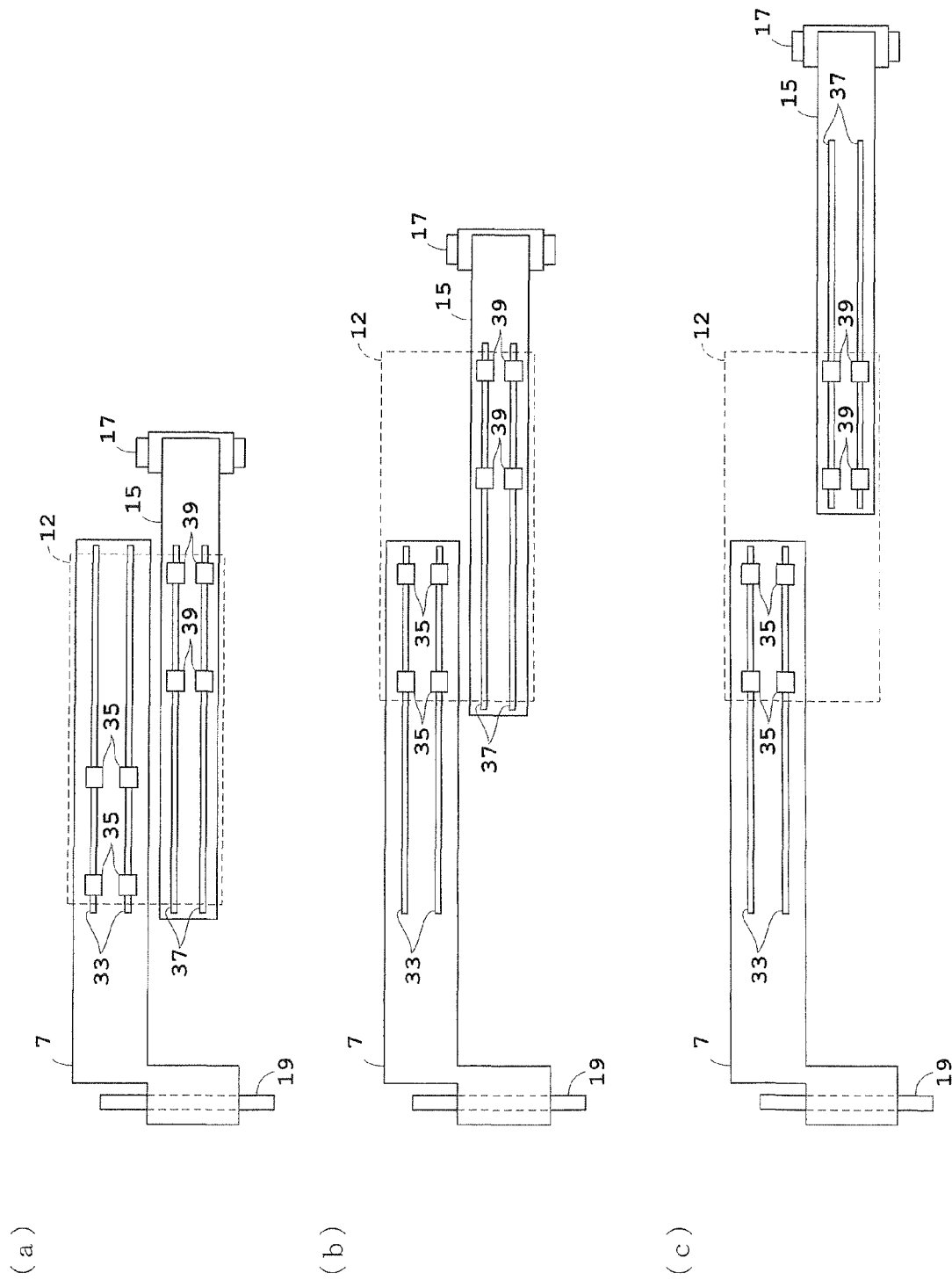
FIG. 6 shows front views of a strut, a middle slider and a support arm according to a modified embodiment, in which (a) shows a state of the middle slider and support arm being retracted, (b) shows a state of the middle slider being extended and the support arm being retracted, and (c) shows a state of the middle slider and support arm being extended.

This invention is not limited to the foregoing embodiment, but may be modified as follows:

(1) In the foregoing embodiment, the strut 7 has the groove A, and is constructed to accommodate the support arm 15 in this groove A when the support arm 15 is retracted. This is not limitative. As shown in FIG. 6, the positions of first and second slide blocks 35 and 39 may be changed so that the moving range of support arm 15 may deviate from the strut 7. With this construction, the strut 7 does not need to have the groove A, which improves rigidity.

Figure 7:
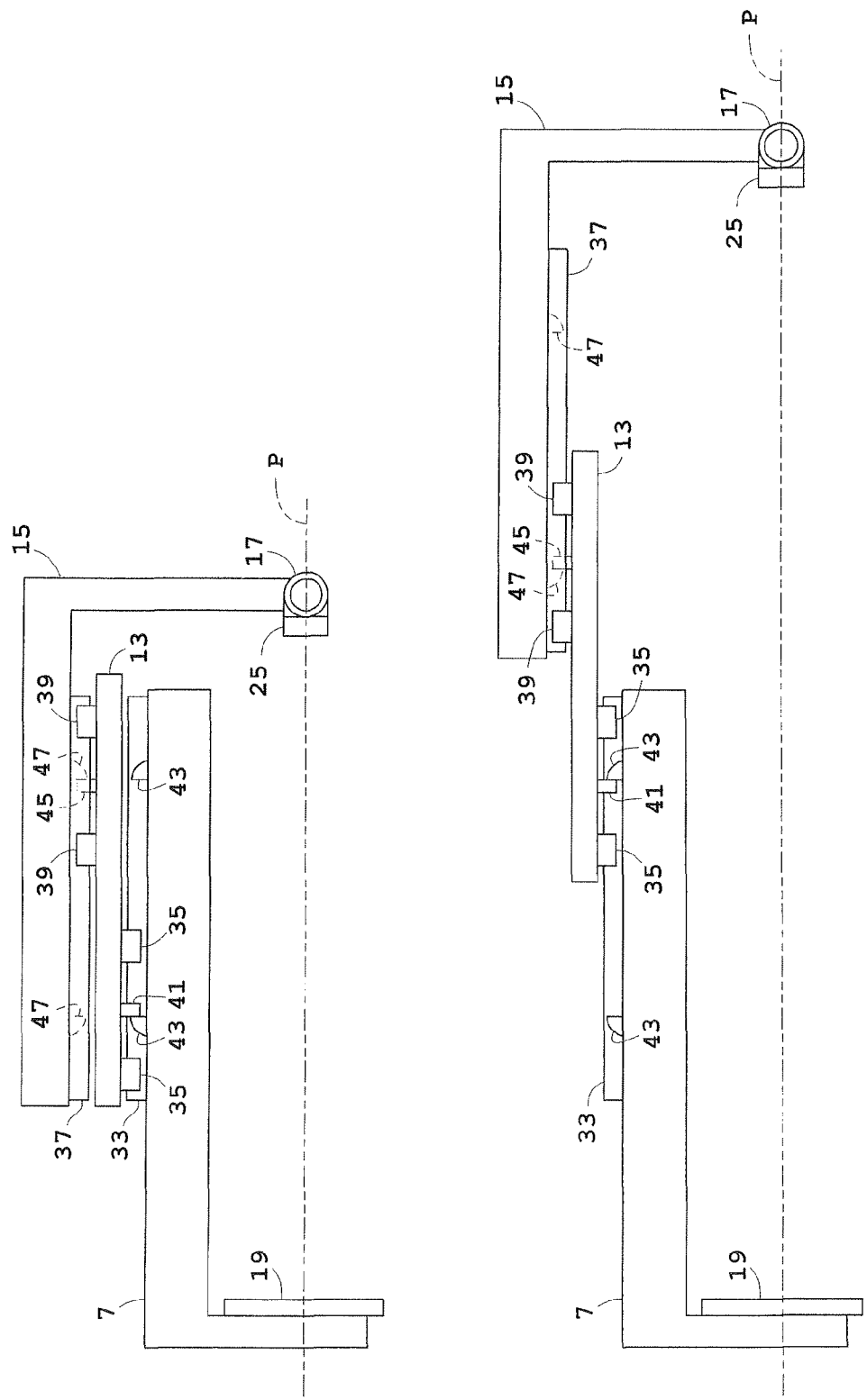
FIG. 7 shows side views of a strut, a middle slider and a support arm according to a modified embodiment, in which (a) shows a state of the middle slider and support arm being retracted, and (b) shows a state of the middle slider and support arm being extended.

The middle slider 11 has all the first and second slide blocks 35 and 39 on one surface thereof, but this is not limitative. As shown in FIG. 7, for example, a middle slider 13 may be constructed to include first slide blocks 35 and second slide blocks 39 arranged on front and back surfaces thereof, respectively.

Figure 8:
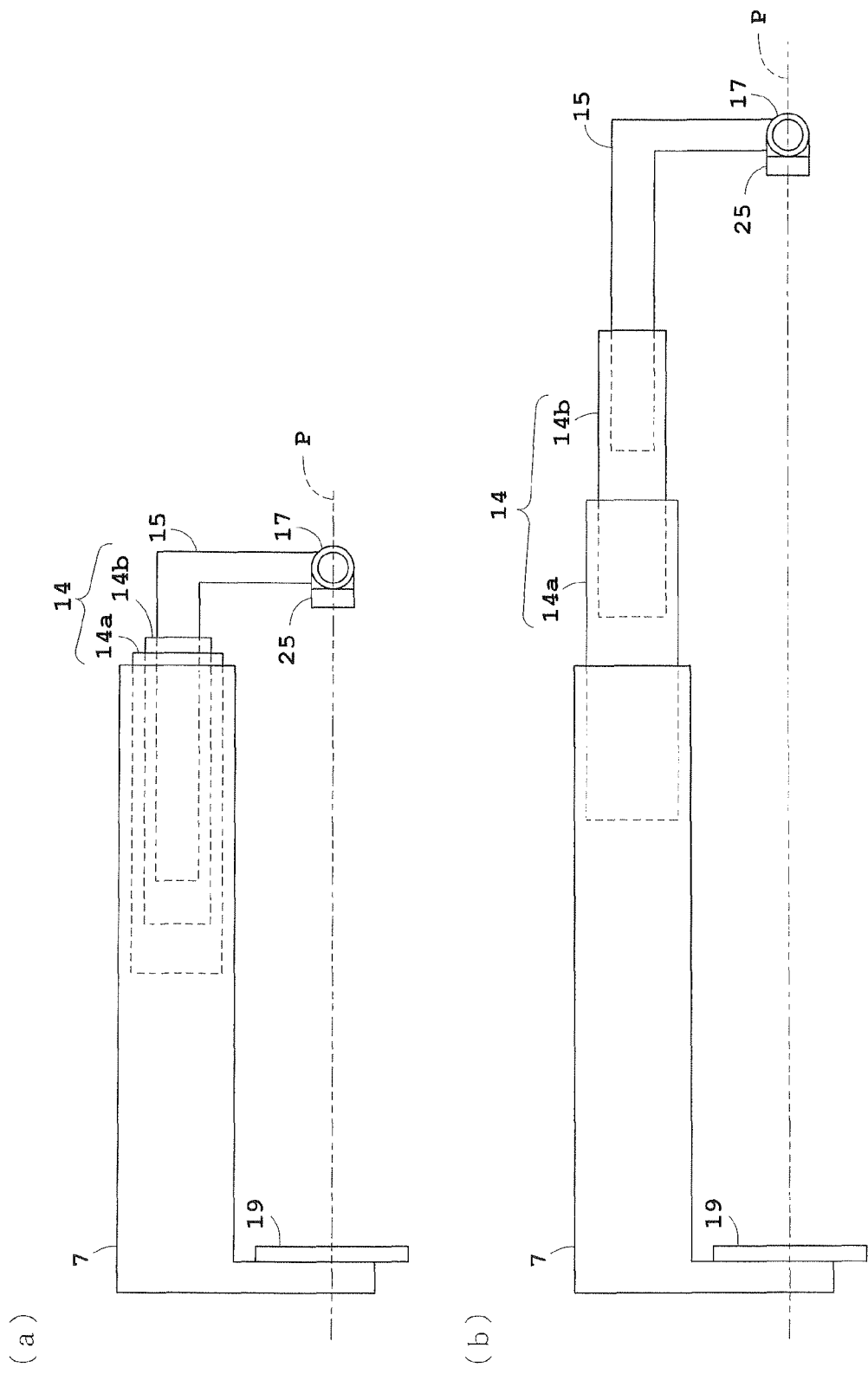
FIG. 8 shows side views of a strut, a middle slider and a support arm according to a modified embodiment, in which (a) shows a state of the middle slider and support arm being retracted, and (b) shows a state of the middle slider and support arm being extended.

Further, the middle slider 11 itself is formed of a plate-like object which does not expand or contract, but this is not limitative. As shown in FIG. 8, for example, a middle slider 14 itself may be constructed telescopic with two, large and small cylindrical split slide members 14a and 14b connected to be slidable relative to each other along the irradiation axis P. The split slide member 14a is held by the strut 7 to be slidable along the irradiation axis P, while the split slide member 14b holds the support arm 15 to be slidable along the irradiation axis P. FIG. 8 illustrates a nesting structure having the split slide members 14a and 14b, strut 7 and support arm 15. With the middle slider 14 itself constructed telescopic in this way, the space between the position where the strut 7 holds the middle slider 14 and the position where the middle slider 14 holds the support arm 15 is extendible and contractible. Thus, the amount of stroke of the X-ray tube 17 is a sum total of the amount of movement of the support arm 15, the amount of movement of the middle slider 14 relative to the strut, and the amount of expansion and contraction of the middle slider 14 itself. Therefore, the amount of stroke of the X-ray tube 17 can be further increased, while curbing installation space.

Figure 9:
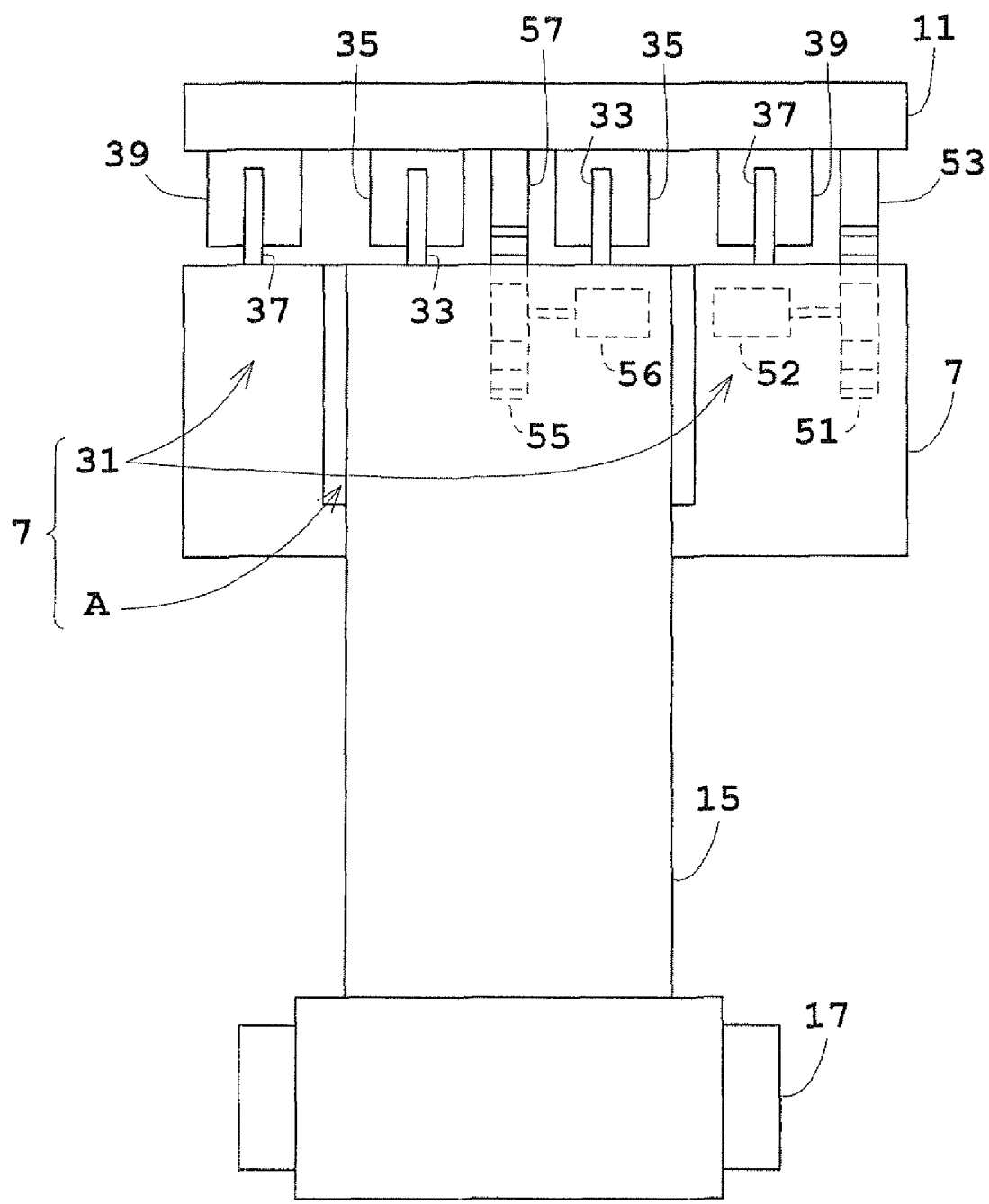
FIG. 9 is a sectional view of a strut, a middle slider and a support arm according to a modified embodiment.
Figure 10:
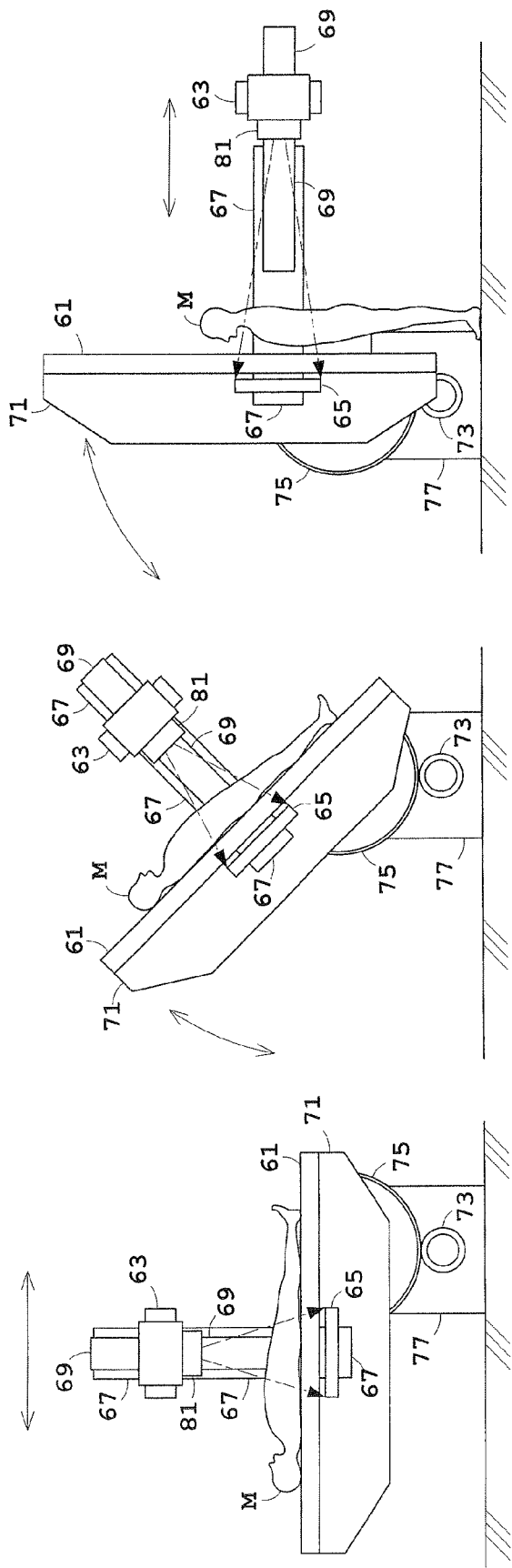
FIG. 10 shows front views of an X-ray fluoroscopic apparatus according to the prior art, in which (a), (b) and (c) show horizontal, inclined and vertical states of a top board, respectively.
Figure 11:
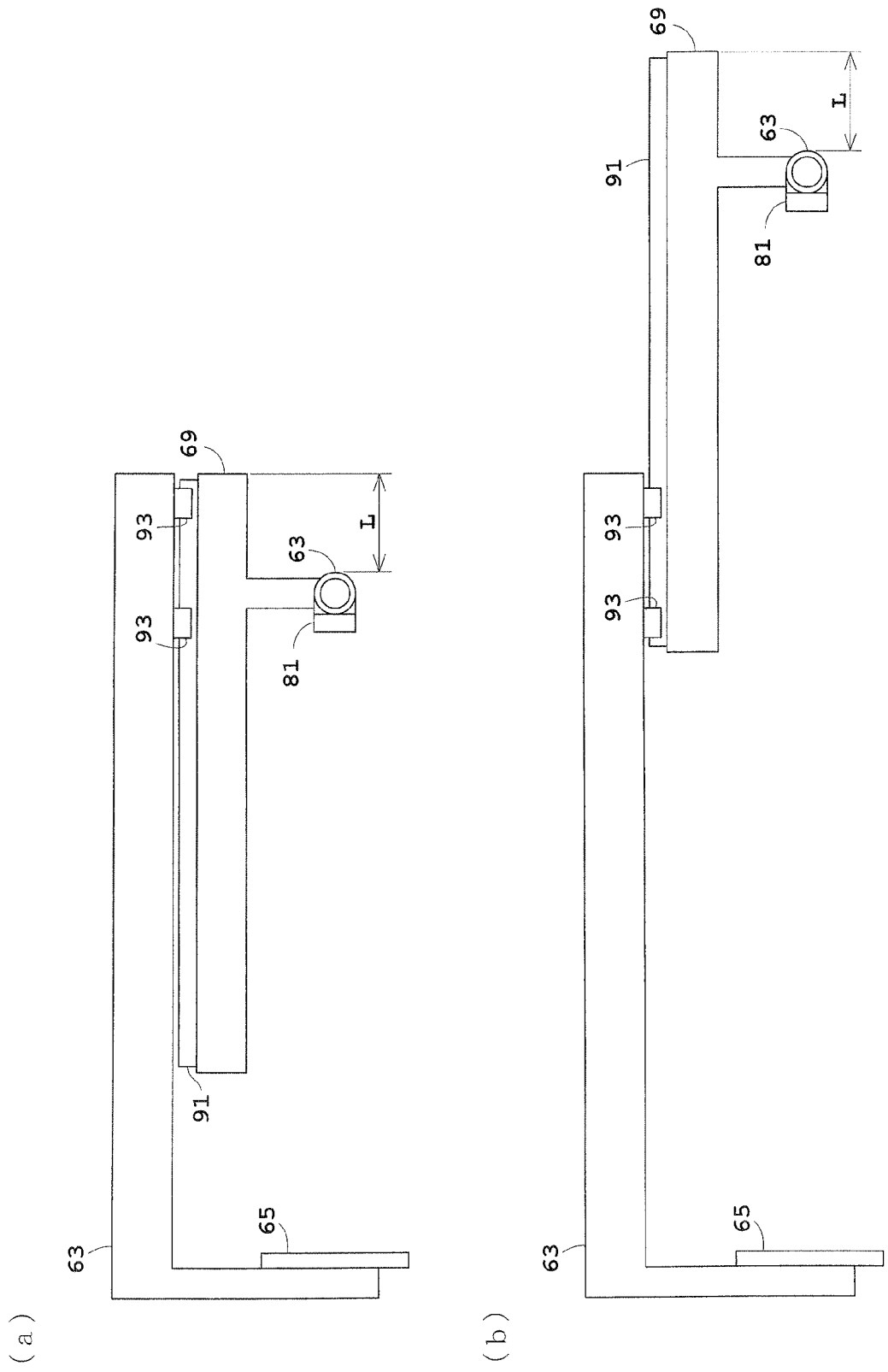
FIG. 11 shows side views of a strut and a support arm according to the prior art, in which (a) shows a state of the support arm being retracted, and (b) shows a state of the support arm being extended.

(2) In the foregoing embodiment, the middle slider 11 and support arm 15 are constructed manually movable by the operator. This is not limitative. As shown in FIG. 9, for example, the strut 7 may include a first gear 51, and a first motor 52 for rotating the first gear 51 in opposite directions, while the middle slider 11 may include a first rack 53 meshed with the first gear 51, whereby the middle slider 11 is movable relative to the strut 7. The support arm 15 may include a second gear 55, and a second motor 56 for rotating the second gear 55 in opposite directions, while the middle slider 11 may include a second rack 57 meshed with the second gear 55, whereby the support arm 15 is movable relative to the middle slider 11. With this construction, the middle slider 11 and support arm 15 can be slid easily. Here, the first gear 51, first motor 52 and first rack 53 correspond to the first drive device in this invention. The second gear 55, second motor 56 and second rack 57 correspond to the second drive device in this invention.

(3) In the foregoing embodiment, the first and second guide mechanisms are formed of the first and second guide rails 33 and 37 and first and second slide blocks 35 and 39. Each may be selected and modified as appropriate as long as it is a mechanism that guides the middle slider or support arm 15 along one axis (irradiation axis P).

(4) In the foregoing embodiment, the first guide rails 33 are provided on the strut 7, but this may be modified to provide them on the middle slider 11. Similarly, although the second guide rails 37 are provided on the support arm 15, this may be modified to provide them on the middle slider 11. In such cases, the arrangement of the first and second slide blocks 35 and 39 also is changed as appropriate.

(5) In the foregoing embodiment, the middle slider 11 has the first and second projections 41 and 45, the leg 31 of the strut 7 has the first restrictors 43, and the support arm 15 has the second restrictors 47. This is not limitative. For example, a modification may be made to provide members on the first and second guide rails 33 and 37 for contacting the first and second slide blocks 35 and 39 to restrict further sliding movement.

(6) In the foregoing embodiment, the imaging device is exemplified by the cassette 19, but this is not limitative. For example, the cassette 19 may be replaced with an imaging device such as a flat panel display or an image intensifier. In this specification, the term focus film distance is used because the cassette 19 is given as an example of imaging device. This is not intended to limit the imaging device to the cassette 19. Where a flat panel display or an image intensifier is used as the imaging device, SID (Source-Image Distance), for example, may be taken into consideration as appropriate.

(7) In the foregoing embodiment, the strut 7 is constructed to hold the cassette 19, but this is not limitative. A cassette support unit may be provided separately from the strut 7 for movably supporting the cassette 19, so that the cassette 19 may move independently of the X-ray tube 17. This can carry out chest radiography conveniently.

The invention claimed is:

1. An X-ray fluoroscopic apparatus for fluoroscoping a patient, comprising an X-ray source for emitting X rays to the patient; a support arm for supporting the X-ray source; a middle slider for holding the support arm to be movable along an irradiation axis of the X-ray source; and a strut for holding the middle slider to be movable along the irradiation axis, the strut having two legs forming ridges thereon to extend along the irradiation axis for holding the middle slider with the legs, and the support arm being insertable into a groove formed between the legs.

2. The X-ray fluoroscopic apparatus according to claim 1, wherein the support arm has a top portion lower than a height of the X-ray source supported by the support arm.

3. The X-ray fluoroscopic apparatus according to claim 1, further comprising a first guide mechanism provided between the strut and the middle slider for guiding the middle slider along the irradiation axis relative to the strut, and a second guide mechanism provided between the middle slider and the support arm for guiding the support arm along the irradiation axis relative to the middle slider.

4. The X-ray fluoroscopic apparatus according to claim 1, further comprising a first drive device for moving the middle slider along the irradiation axis relative to the strut, and a second drive device for moving the support arm along the irradiation axis relative to the middle slider.

5. The X-ray fluoroscopic apparatus according to claim 1, wherein the middle slider has a plurality of split slide members, the split slide members being connected to each other to be movable along the irradiation axis, such that a space between a position where the strut holds the middle slider and a position where the middle slider holds the support arm is extendible and contractible.

6. The X-ray fluoroscopic apparatus according to claim 1, wherein the strut is rotatable about a horizontal axis.

7. The X-ray fluoroscopic apparatus according to claim 1, further comprising a first projection provided on one of the strut and the middle slider, and first restrictors provided on the other of the strut and the middle slider to be capable of contacting the first projection, for limiting a moving range of the middle slider relative to the strut, and a second projection provided on one of the middle slider and the support arm, and second restrictors provided on the other of the middle slider and the support arm to be capable of contacting the second projection, for limiting a moving range of the support arm relative to the middle slider.

* * * * *